(12) United States Patent
Kolpashchikov

(10) Patent No.: US 8,551,768 B2
(45) Date of Patent: Oct. 8, 2013

(54) SPLIT DNA ENZYME FOR VISUAL SINGLE NUCLEOTIDE POLYMORPHISM TYPING

(75) Inventor: Dmitry Kolpashchikov, Winter Park, FL (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/130,536

(22) PCT Filed: Nov. 20, 2009

(86) PCT No.: PCT/US2009/065341
§ 371 (c)(1),
(2), (4) Date: Aug. 8, 2011

(87) PCT Pub. No.: WO2010/059944
PCT Pub. Date: May 27, 2010

(65) Prior Publication Data
US 2012/0135539 A1    May 31, 2012

Related U.S. Application Data

(60) Provisional application No. 61/117,081, filed on Nov. 21, 2008.

(51) Int. Cl.
| | |
|---|---|
| C12M 3/00 | (2006.01) |
| C12M 1/34 | (2006.01) |
| C12Q 1/68 | (2006.01) |
| C12Q 1/28 | (2006.01) |
| G01N 33/53 | (2006.01) |
| B01L 3/00 | (2006.01) |
| G01N 33/566 | (2006.01) |
| C07H 21/02 | (2006.01) |
| C07H 21/04 | (2006.01) |

(52) U.S. Cl.
USPC ............... 435/287.2; 435/6.1; 435/707.28; 435/192; 435/6.11; 422/430; 436/501; 536/23.1; 536/24.3

(58) Field of Classification Search
USPC ............... 435/6.1, 6.11, 7.7, 28, 192, 287.2; 422/430; 436/501; 536/23.1, 24.3
See application file for complete search history.

(56) References Cited

U.S. PATENT DOCUMENTS

| | | |
|---|---|---|
| 6,413,722 B1 | 7/2002 | Arnold et al. |
| 2002/0172960 A1 | 11/2002 | Bao et al. |

(Continued)

FOREIGN PATENT DOCUMENTS

| | | |
|---|---|---|
| WO | 92/20823 A1 | 11/1992 |
| WO | 2007115242 A2 | 10/2007 |

(Continued)

OTHER PUBLICATIONS

Pavlov et al, Amplified Chemiluminescence Surface Detection of DNA and Telomerase Activity Using Catalytic Nucleic Acid Labels, 2004, Anal. Chem., 76, 2152-2156.*

(Continued)

Primary Examiner — Narayan Bhat
(74) Attorney, Agent, or Firm — Evans & Molinelli PLLC; Judith Evans

(57) ABSTRACT

A probe that changes solution color in the presence of only one of the two DNA sequences, which differ by a single nucleotide, is reported. The probe consists of two oligodeoxyribonucleotides, which form a hydrogen peroxidase-like DNA enzyme when hybridized to the abutting fragments of the complementary analyte. The active peroxidase catalyses oxidation of colorless substrates to the colored products. The probe allows visual detection of a mutation in Alzheimer's disease-related DNA.

21 Claims, 5 Drawing Sheets

(56) References Cited

U.S. PATENT DOCUMENTS

2006/0110739 A1* 5/2006 Heyduk et al. .................. 435/6
2007/0231810 A1 10/2007 Todd et al.

FOREIGN PATENT DOCUMENTS

WO 2008/054834 A2 5/2008
WO 2010/059944 A1 5/2010

OTHER PUBLICATIONS

ISA/US, "International Preliminary Report on Patentability for corresponding international application No. PCT/US2009/065341", May 24, 2011, pp. 1-6.
ISA/US, "International Search Report and Written Opinion for corresponding international application No. PCT/US09/65341", Feb. 25, 2010, pp. 1-10.
Dmitry M. Kolpashchikov, "Split DNA Enzyme for Visual Single Nueleotide Polymorphism Typing", "Journal of American Chemical Society", Mar. 12, 2008, pp. 2934-2935, vol. 130, No. 10.
Babendure et al., "Aptamers Switch on Fluorescence of Triphenylmethane Dyes", "J. Am. Chem. Soc.", Nov. 8, 2003, pp. 14716-14717, vol. 125, Publisher: American Chemical Society, Published in: US.
Bonnet et al, "Thermodynamic basis of the enhanced specificity of structured DNA probes", "Proc. Natl. Acad. Sci.", May 1999, pp. 6171-6174, vol. 96, Published in: US.
Kolpashchikov, Dmitry M., "Binary Malachite Green Aptamer for Fluorescent Detection of Nucleic Acids", Aug. 19, 2005, pp. 12442-12443, vol. 127, Publisher: American Chemical Society, Published in: US.
Kolpashchikov, Dmitry M., "A Binary DNA Probe for Highly Specific Nucleic Acid Recognition", "J. Am. Chem. Soc.", Jul. 21, 2006, pp. 10625-10628, vol. 128, Publisher: American Chemical Society, Published in: US.
Kolpashchikov, Dmitry M., "A Binary Deoxyribozyme for Nucleic Acid Analysis", "ChernBioChern", 2007, pp. 2039-2042, vol. 8, Publisher: Wiley-VCH Verlag GmbH & Co., Published in: Germany.

Tyagi et al, "Molecular Beacons: Probes that Fluoresce upon Hybridization", "Nature Biotechnology", Mar. 1996, pp. 303-308, vol. 14, Publisher: Nature Publishing Group.
Marras et al, "Real-time assays with molecular beacons and other fluorescent nucleic acid hybridization probes", "Clinica Chimica Acta", Aug. 18, 2005, pp. 48-60, vol. 363, Publisher: Elsevier B.V.
Mokany et al., "MNAzymes, a Versatile New Class of Nucleic Acid Enzymes That Can Function as Biosensors and Molecular Switches", "J. Am. Chem. Soc.", 2010, pp. 1051-1059, vol. 132, No. 3, Publisher: American Chemical Society.
ISA, "International Preliminary Report on Patentability for Corresponding International Application No. PCT/US2010/022428", Aug. 2, 2011, pp. 1-8, Published in: Switzerland.
ISA, "International Search Report and Written Opinion for Corresponding International Application No. PCT/US10/22428", Mar. 19, 2010, pp. 1-12, Published in: US.
Sando et al., "Light-Up HoechstDNA AptamerPair: Generation of an Aptamer-Selective Fluorophore from a Conventional DNA-Staining Dye", "ChemBioChem", 2007, pp. 1795-1803, vol. 8, Publisher: Wiley-VCH Verlag GmbH & Co., Published in: Germany.
Deng, M. et al., "Highly Effective Colormetric and Visual Detection of Nucleic Acids Using an Asymmetrically Split Peroxidase DNAzyme", J. Am. Chem. Soc., 2008, v.130 (39), pp. 13095-13102. American Chemical Society. http://pubs.acs.org/doi/abs/10.1021/ja803507d.
Xiao, Y. et al., "Lighting Up Biochemiluminescence by the Surface Self-Assembly of DNA-Hemin Complexes", ChemBioChem, 2004, v.5, (3), pp. 374-379. http://onlinelibrary.wiley.com/doi/10.1002/cbic.200300794/abstract.
Travasico, P., et al., "A ribozyme and a catalytic DNA with peroxidase activity: active sites versus cofactor-binding sites", Chemistry & Biology, 1999, v. 6 (11), pp. 779-787. Canada. XP55036481 http://www.cell.com/chemistry-biology/abstract/S1074-5521%2899%2980125-2.
Supplementary European Search Report and Written Opinion for EP 09828292. European Patent Office. Munich, Germany, pp. 1-9. Sep. 9, 2012.

* cited by examiner

SEQUENCE LISTING

<160> NUMBER OF SEQ ID NOS: 12

<210> SEQ ID NO 1
<211> LENGTH: 34
<212> TYPE: DNA
<213> ORGANISM: Homo sapiens

<400> SEQUENCE: 1
tggcttcgcc cagggtacac caggacacgg tttt                     34

<210> SEQ ID NO 2
<211> LENGTH: 34
<212> TYPE: DNA
<213> ORGANISM: Homo sapiens

<400> SEQUENCE: 2
tggcttcgcc cagggtgcac caggacacgg tttt                     34

<210> SEQ ID NO 3
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 3 gggtaggg                                                   8

<210> SEQ ID NO 4
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 4 gggttggg                                                   8

<210> SEQ ID NO 5
<211> LENGTH: 3
<212> TYPE: DNA
<213> ORGANISM: Artificial Sequence
<220> FEATURE:
<223> OTHER INFORMATION: Synthetic oligonucleotide

<400> SEQUENCE: 5 ggg                                                        3

<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 6
gggcgggttg gg                                              12

<210> SEQ ID NO 7
<211> LENGTH: 12
<212> TYPE: DNA
<213> ORGANISM: Artificial Sequence
<220> FEATURE:
<223> OTHER INFORMATION: Synthetic oligonucleotide

```
<400> SEQUENCE: 7
gggtagggcg gg                                                          12

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
gggtagggcg ggttggg                                                     17

<210> SEQ ID NO 9
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 9
ccgtgtcctg                                                             10

<210> SEQ ID NO 10
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 10 gtgcaccc                                                                8

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: Location of dithymidine linkers

<400> SEQUENCE: 11
ccgtgtcctg gggtaggg                                                    18

<210> SEQ ID NO 12
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(9)
<223> OTHER INFORMATION: Location of dithymidine linkers

<400> SEQUENCE: 12
gggttggggt gcaccc                                                      16
```

US 8,551,768 B2

SPLIT DNA ENZYME FOR VISUAL SINGLE NUCLEOTIDE POLYMORPHISM TYPING

CROSS-REFERENCE TO RELATED APPLICATIONS

This application claims benefit of Provisional Appln. 61/117,081, filed Nov. 21, 2008, the entire contents of which are hereby incorporated by reference as if fully set forth herein, under 35 U.S.C. §119(e).

STATEMENT OF GOVERNMENTAL INTEREST

This invention was made with Government support under NIH, NHGRI R21 HG004060. The Government has certain rights in the invention.

BACKGROUND OF THE INVENTION

1. Field of the Invention

The present invention relates to binary probes for detecting nucleic acids.

2. Description of the Related Art Invention

Single nucleotide polymorphisms (SNPs) are the most abundant forms of genetic variations in the human genome. Large-scale sequence analysis is needed for a population-based genetic risk assessment and diagnostic tests once a mutation has been identified. However, most of the methods for SNP screening require enzymatic manipulations such as endonuclease digestion, ligation or primer extension, and often separation of the resultant products.[1] These labor intensive and time consuming procedures are some of the biggest impediments to moving SNP typing techniques to point-of-care settings, which require straightforward, inexpensive, and disposable detection formats. Towards fulfilling of these requirements a probe for visual SNP detection was developed in this study.

Binary probes for fluorimetric analysis of single nucleotide substitutions were developed earlier.[2] The probes demonstrate improved selectivity in comparison with conventional hybridization-based approaches, since the two parts of the probes form relatively short (7-10 nucleotide) duplexes with target sequences. These short hybrids are extremely sensitive to single nucleotide substitutions at room temperature and generate high fluorescent signal only in the presence of the fully complementary targets. Binary probes do not require precise temperature control for SNP typing.[2d,e] However, a fluorimeter is required for signal registration.

Earlier, gold nanoparticle (GNP)—based approaches were suggested for SNP typing with a colorimetric/optical outcome.[7] These methods involve attaching of non-complementary DNA oligonucleotides capped with thiol groups to the surface of two batches of 13-nm GNPs. When DNA, which is complementary to the two engrafted sequences, is added to the solution, a polymer network is formed. This condensed network brought the conjugated GNPs to self-assemble into aggregates with a concomitant red-to-purple color change. Alternatively, a non-crosslinking DNA-GNP aggregation method takes advantage of blunt end stacking interactions of the DNA double helixes.[8a] All these approaches demand conjugation of DNA probes with colloid gold. In addition, some of the techniques require precise temperature control for allele discrimination. These procedures complicate both the probe preparation and the assay itself. Unlike gold nanoparticle-based approaches, a binary DNA peroxidase probe requires neither postsynthetic modification of the probe oligonucleotides, nor precise temperature control for SNP typing.

There is still a need for a DNA probe that retains sensitivity while permitting visual detection of a DNA analyte.

BRIEF DESCRIPTION OF THE DRAWINGS

The present invention is illustrated by way of example, and not by way of limitation, in the figures of the accompanying drawings and in which like reference numerals refer to similar elements.

DEFINITIONS

Figure 1:
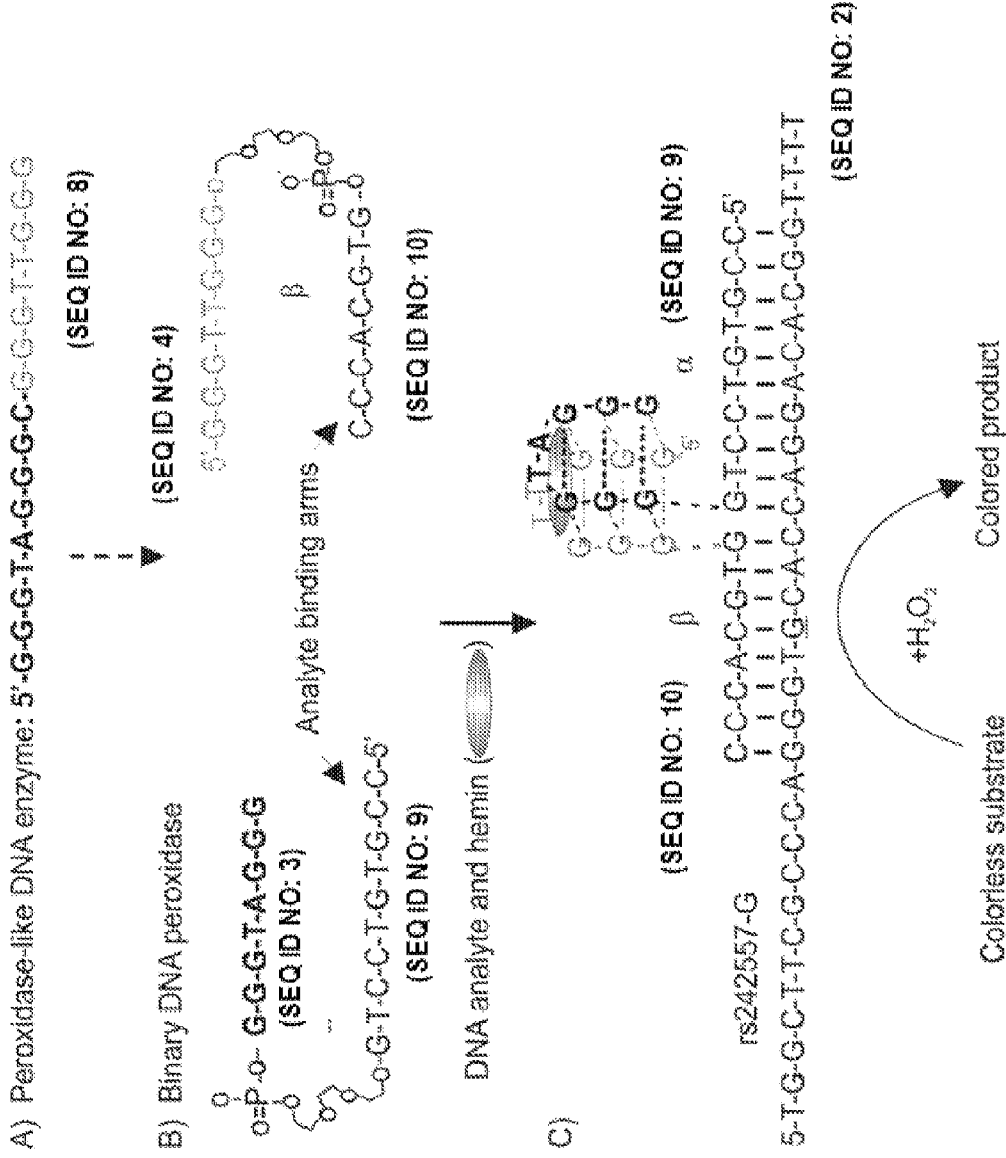
FIG. 1. Design of the binary DNA peroxidase for SNP analysis. A: Parent peroxidase-like DNA enzyme. B: Binary DNA peroxidase probe. C: The probe forms active peroxidase upon hybridizing to the abutting positions of the analyte. The enzyme catalyzes oxidation of a colorless substrate to colored products. The triethylenglycol linkers are shown as dashed lines in panel C. The SNP site in the analyte sequence is underlined.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G (as well as U) may occasionally participate in base pairings. Nucleotides that normally pair up when DNA or RNA adopts a double stranded configuration may also be referred to herein as "complementary bases".

"Complementary nucleotide sequence" here generally refers to a sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the analyte and analyte-binding arm on the binary probes should be exact, 100%. If less selectivity is required, then routine experimentation will determine the level of complementarity that provides the desired result.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different or unusual sugars (i.e. sugars other than the "usual" pentose), or a combination of the two. Nucleotide analogs of DNA or RNA can be used to make binary probes. Examples of nucleotide analogs useful according to the present invention include those listed in the approved listing of modified bases at 37 CFR .sctn.1.822 (which is incorporated herein by reference). Other useful analogs include those described in published international application no. WO 92/20823 (the disclosures of which are incorporated herein by reference), or analogs made according to the methods disclosed therein.

"Oligonucleotide or polynucleotide" generally refers to a polymer of single-stranded nucleotides. As used herein, "oligonucleotide" and its grammatical equivalents will include the full range of nucleic acids. An oligonucleotide will typically refer to a nucleic acid molecule comprised of a linear strand of deoxy- and ribonucleotides.

Binary probe means two molecules or one molecule containing two distinct parts that recognizes a specific sequence in a DNA or RNA analyte, and which, only upon recognition and binding to the analyte, generates a detectable signal such as fluorescence, luminescescence or a visible color change such as in the case of the present binary oligonucleotide peroxidase probe (BOPP).

Hemin (trade name Panhematin) is an iron-containing porphyrin.[1] that is used in the management of porphyria attacks, particularly in acute intermittent porphyria. It is sometimes distinguished from "Hematin", which is hemoglobin with iron in ferric state. However, the terms are sometimes equated.[2]

Aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers can be used for both basic research and clinical purposes as macromolecular drugs. Aptamers can be combined with ribozymes to self-cleave in the presence of their target molecule.

Peroxidase-like activity means that the molecule (DNA enzyme) catalysis hydrogen peroxide decomposition, similar to that of horseradish peroxidase. Peroxidases are a large family of enzymes that typically catalyze a reaction of the form: $ROOR'+$electron donor $(2\ e^-)+2H^+ \rightarrow ROH+R'OH$. For many of these enzymes such as the one modified in the present probe, the optimal substrate is hydrogen peroxide. Colored reaction products allow detection of the enzyme with high sensitivity.

In various embodiments, the binary probe of the present invention may combine one or more modifications or mutations including additions, deletions, and substitutions. These mutations may, for example, change the length of, or alter the nucleotide sequence of, a loop, a spacer region or a recognition sequence (or domain). Modification or mutation of the recognition site via well-known methods allows one to alter the sequence specificity of an enzymatic nucleic acid molecule.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35 40° C., with 37° C. being particularly preferred, as well as a pH of about 7.0 8.0, with 7.5 being particularly preferred, and further comprise the availability of cations, preferably divalent and/or monovalent cations, with a concentration of about 2 15 mM $Mg2+$ and 0 1.0 M $Na+$ being particularly preferred.

In the following description, for the purposes of explanation, numerous specific details are set forth in order to provide a thorough understanding of the present invention. It will be apparent, however, to one skilled in the art that the present invention may be practiced without these specific details.

DETAILED DESCRIPTION

We have discovered a new binary oligonucleotide (DNA or RNA or both) peroxidase probe (hereafter "BOPP") capable of recognizing SNPs with extremely high sensitivity. The BOPP acquires peroxidase-like activity after it hybridizes to a specific target DNA or RNA analyte, which causes the BOPP to form a guanine-quadruplex that binds hemin. Hemin bound to the guanine quadruplex (G-quadruplex) demonstrates hydrogen peroxidase-like activity that is ~250 times greater than unbound hemin. Specifically, the BOPP is a non-naturally occurring binary oligonucleotide peroxidase probe for detecting a single stranded oligonucleotide analyte comprising two antiparallel oligonucleotide strands, wherein
 a first oligonucleotide strand comprises:
  a. at its 5'-terminus an oligonucleotide hemin-binding arm
   (that is optionally flanked by a linker)

b. an optional linker that is flanked by a first oligonucleotide analyte binding arm, and
c. at its 3'-terminus, the first oligonucleotide analyte binding arm that is complementary to and selectively hybridizes with a first region of the oligonucleotide analyte, and
2. a second oligonucleotide strand comprises:
a. at its 3'-terminus an oligonucleotide hemin-binding arm that is flanked by an optional linker,
b. an optional linker that is flanked by a first oligonucleotide analyte binding arm, and
c. at its 5'-terminus, a second oligonucleotide analyte binding arm that is complementary to and selectively hybridizes with a second region of the oligonucleotide analyte.

In certain embodiments, there is enough flexibility in the hemin- and analyte-binding arms of the oligonucleotide strands of the probe so that a linker between the two is not needed in order for the probes to form a four-way junction with target analyte. The BOPP was based on a peroxidase-like hemin binding DNA aptamer shown in FIG. 1A that was obtained earlier by in vitro selection.[3] When the aptamer binds to hemin, it forms a guanine quartet (herein a quanine-quadruplex or G-quadruplex) that demonstrates hydrogen peroxidase-like activity that is ~250 times greater than hemin alone.[4] This DNA enzyme aptamer was used for the design of allosterically regulated sensors for nucleic acids, AMP and lysozyme that allow colorimetric or luminescent readouts.[5] Hemin is a porphyrin, a small molecule, that binds to G-quadruplex of the BOPP noncovalently, by stacking and hydrophobic interactions. However, the covalent binding of one or both of the antiparallel oligonucleotide strands of the probe to hemin will increase the sensitivity of the assay. The mechanism by which the association of hemin with the G-quadruplex increases the peroxidase activity of the hemin is unknown. Without being bound by theory, the hydrophobic environment of G-quadruplex may increase the affinity of hemin for hydrogen peroxide.

To form the G-quadruplex, the hemin arms can be configured differently as follows: the oligonucleotide hemin-binding arm on the first oligonucleotide strand can comprise 3' gggatggg 5'(SEQ ID NO: 3), and the oligonucleotide hemin-binding arm on the second oligonucleotide strand can comprises 5' gggttggg 3'(SEQ ID NO: 4); or the oligonucleotide hemin-binding arm on the first oligonucleotide strand can comprise 3'ggg 5'(SEQ ID NO: 5), and the oligonucleotide hemin-binding arm on the second oligonucleotide strand can include 5'gggcgggttggg 3'(SEQ ID NO: 6); or the oligonucleotide hemin-binding arm on the first oligonucleotide strand can comprise 3'gggcgggatggg 5'(SEQ ID NO: 7), and the oligonucleotide hemin-binding arm on the second oligonucleotide strand can include 5'ggg 3'(SEQ ID NO: 5).

The present invention is described in Kolpashchikov D. M. (2008). "Split DNA enzyme for visual single nucleotide polymorphism typing." JACS, 130, 2934-2935, incorporated herein by reference. To construct the BOPP, we split the sequence of the peroxidase-like hemin-binding DNA enzyme (FIG. 1A) into two antiparallel oligonucleotide strands and removed the deoxycytidine was removed. (Notice the one C residue in the middle of the enzyme sequence shown in FIG. 1A that is not present in the modified enzyme shown in FIG. 1B, α strand). Analyte binding arms were added to each of the two antiparallel oligonucleotide strands (to the 3' end of one strand and to the 5' end of the other strand) via a flexible linker such as triethylenglycol (FIG. 1). The analyte can be DNA or RNA with the analyte binding arms being designed accordingly. In the absence of nucleic acid analyte, the two oligonucleotide strands of the BOPP exist predominantly in the dissociated form (at certain concentrations and buffer conditions). When the analyte binding arms hybridize to the respective adjacent positions on the target DNA or RNA analyte, the free end of the strand (made from the DNA hemin-binding aptamer) forms a guanine quadruplex (hereafter "G-quadruplex") structure that acquires peroxidase activity when bound to hemin (FIG. 1C). The BOPP bound to hemin is an active peroxidase that catalyzes the oxidation of a colorless substrate to a colored product that can be detected both visually and spectrophotometrically.

To test the specificity of the probe and the visual signal, we used as a model analyte an SNP that is a part of the coding sequence for microtubule associated protein tau (MAPT). The hyplotype H1c -carrying an SNP rs242557 G to A substitution at the MAPT locus has been shown to be associated with increased risk of developing Alzheimer's disease.[6] Therefore, the analyte binding arms of the BOPP were tailored to recognize the major allele rs242557-G SEQ ID NO: 2 (FIGS. 1 B and C).

Figure 2:
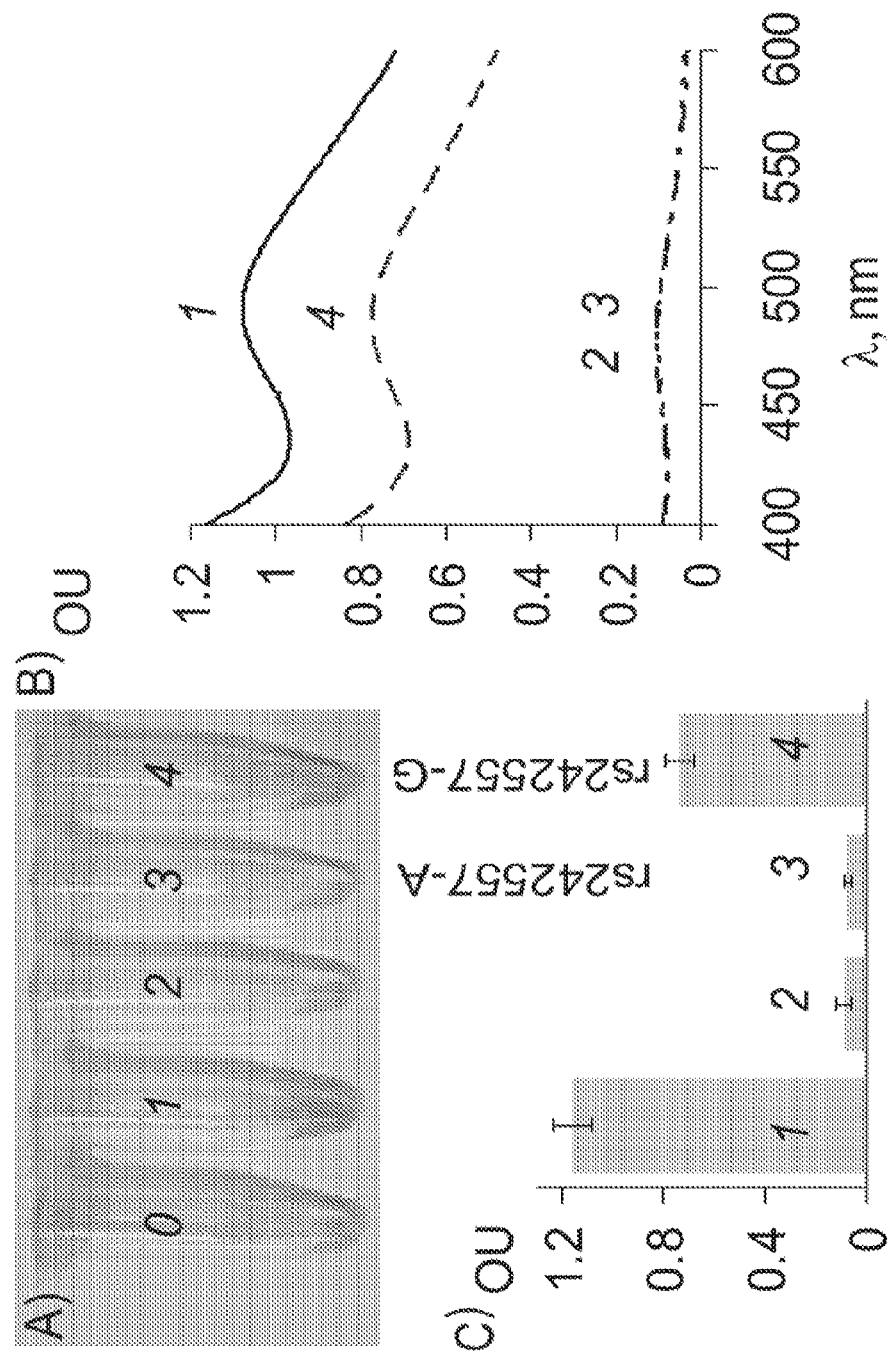
FIG. 2. Binary DNA peroxidase probe reports single nucleotide substitution in tau protein coding DNA. A: Visual detection. Sample 0: reaction buffer (50 mM HEPES, pH 7.4, 50 mM $MgCl_2$, 20 mM KCl, 120 mM NaCl, 0.03% Triton X-100, 1% DMSO, hemin (125 nM), $H_2O_2$ (1 mM), and DAB (1 mM)); Sample 1: reaction buffer in the presence of 1 µM peroxidase-like DNA enzyme (positive control). Strands α and β (1 µM) in the absence (sample 2), or presence of 1 µM rs242557-A SEQ ID NO: 1 (TGG CTT CGC CCA GGG TAC ACC AGG ACA CGG TTT T) (sample 3), or 1 µM rs242557-G SEQ ID NO: 2 (TGG CTT CGC CCA GGG TGC ACC AGG ACA CGG TTT T) (sample 4); The samples were incubated 30 min at room temperature. B: Electron spectrum of the same samples; sample 0 was used as a reference. C: Average optical densities at 500 nm of five independent measurements.

FIG. 2 demonstrates the change of light absorption of the solution containing the BOPP when 3-3'-diaminobenzidine tetrahydrochloride (DAB) was used as an oxidizable substrate. The solution turned brown in the presence of 1 μM rs242557-G, but not in the presence of rs242557-A SEQ ID NO: 1 that contained just a single nucleotide mismatch (compare 4 with 3 in FIG. 2A). The light absorption in the presence of the mismatched target was as low as in the absence of any analyte (compare 3 with 2 in panels B and C). At the same time, high absorption was observed in the presence of complementary target (sample 4, B and C). The signal-to-background ratio (S/B) was ~10 after 30 min of incubation. This signal was only ~38% lower than that of the solution containing the parent peroxidase-like DNA enzyme (sample 1).

Figure 3:
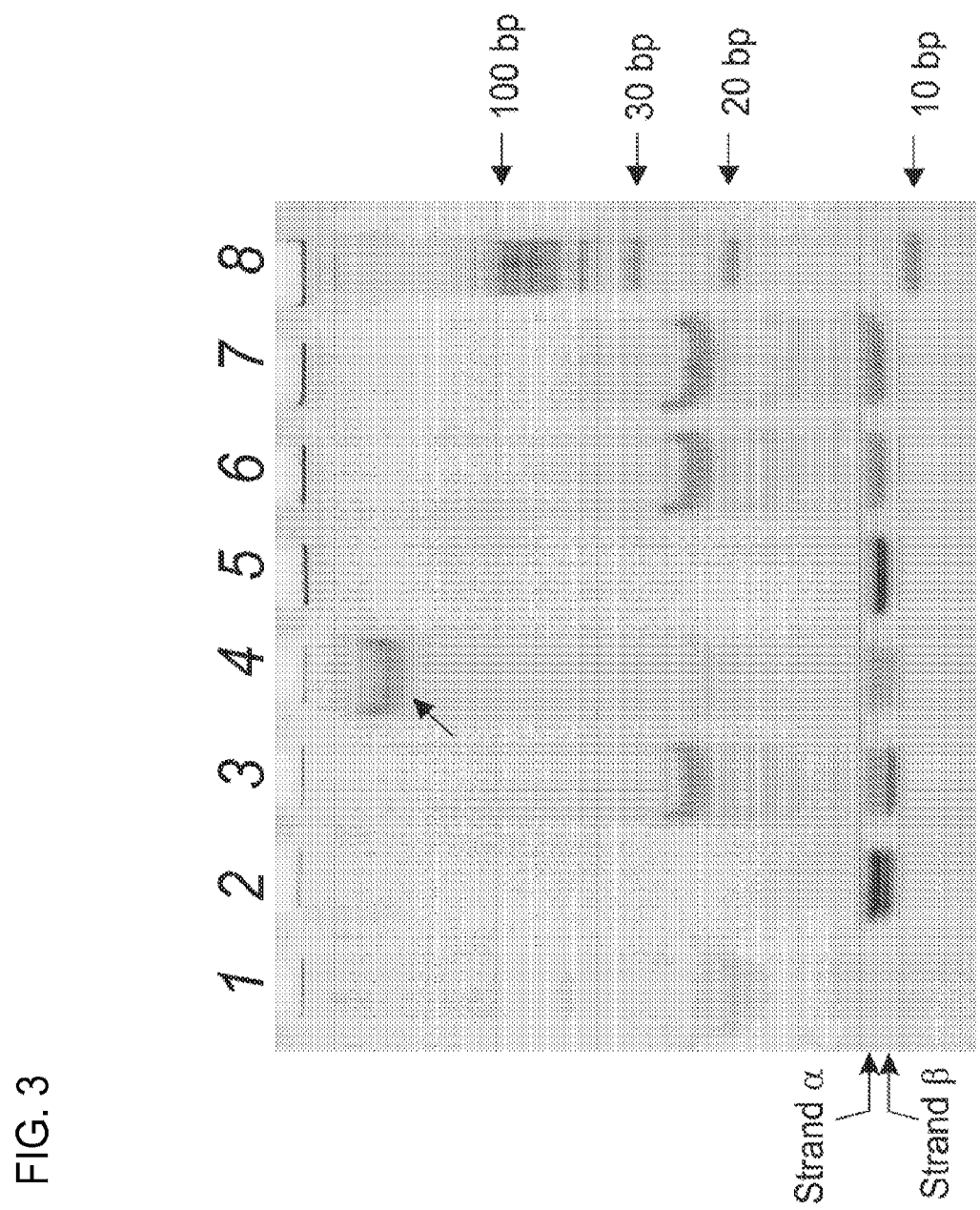
FIG. 3. Analysis of binary DNA peroxidase probe by native 12% PAGE. All samples contained the reaction buffer (see legend to FIG. 2). In addition, following oligonucleotides were added. Lane 1: Peroxidase-like DNA enzyme (1 µM); lane 2: Binary DNA peroxidase (1 µM both strands); lane 3: Binary DNA peroxidase (1 µM both strands) and rs242557-A (1 µM); lane 4: Binary DNA peroxidase (1 µM both strands) and rs242557-G (1 µM); lane 5: Strand α (1 µM) only; lane 6: Strand α (1 µM) and rs242557-A (1 µM); lane 7: Strand α (1 µM) and rs242557-G (1 µM); 8: 10 base pairs (10 bp) DNA ladder. The low mobility band in lane 4 is indicated by an arrow.

To further verify the mechanism of probe activation upon hybridization to fully complementary target (FIG. 1), samples 1-4 were analyzed by native PAGE (FIG. 3, lanes 1-4). In the absence of an analyte the first and second oligonucleotide strands designated α and β, migrate as two separate bands (lane 2). This proves that the two components of the BOPP exist predominantly in the dissociated form in the absence of the specific target analyte. At the same time a low mobility band, which migrates above 100 base pair (bp) DNA marker, was observed only in the presence of rs242557-G SEQ ID NO: 2 (lane 4), but not in the presence of rs242557-A SEQ ID NO: 1 (lane 3) which has a single nucleotide mismatch from the intended target DNA. This band can be attributed to the tripartite complex depicted in FIG. 1C which is composed of the BOPP bound to both hemin and the target analyte. The unexpectedly low mobility of this 68-nucleotide associate can be explained by the binding of the positively charged hemin, which increases the molecular weight and reduces the negative charge of the complex. The significant gel retardation of the parent 17-mer DNA peroxidase, which is also bound to hemin, (lane 1) supports this suggestion. It should also be mentioned that strand α hybridizes both to rs242557-G and rs242557-A even in the absence of strand β, thus forming the 52-nucleotide DNA associate, which migrates between 20 and 30 by markers (lanes 3, 4, 6 and 7). The faint band below 20 bp marker in lanes 3, 6, and 7 corresponds to the mobility of the 34-nucleotide rs242557-G or rs242557-A.

Figure 4:
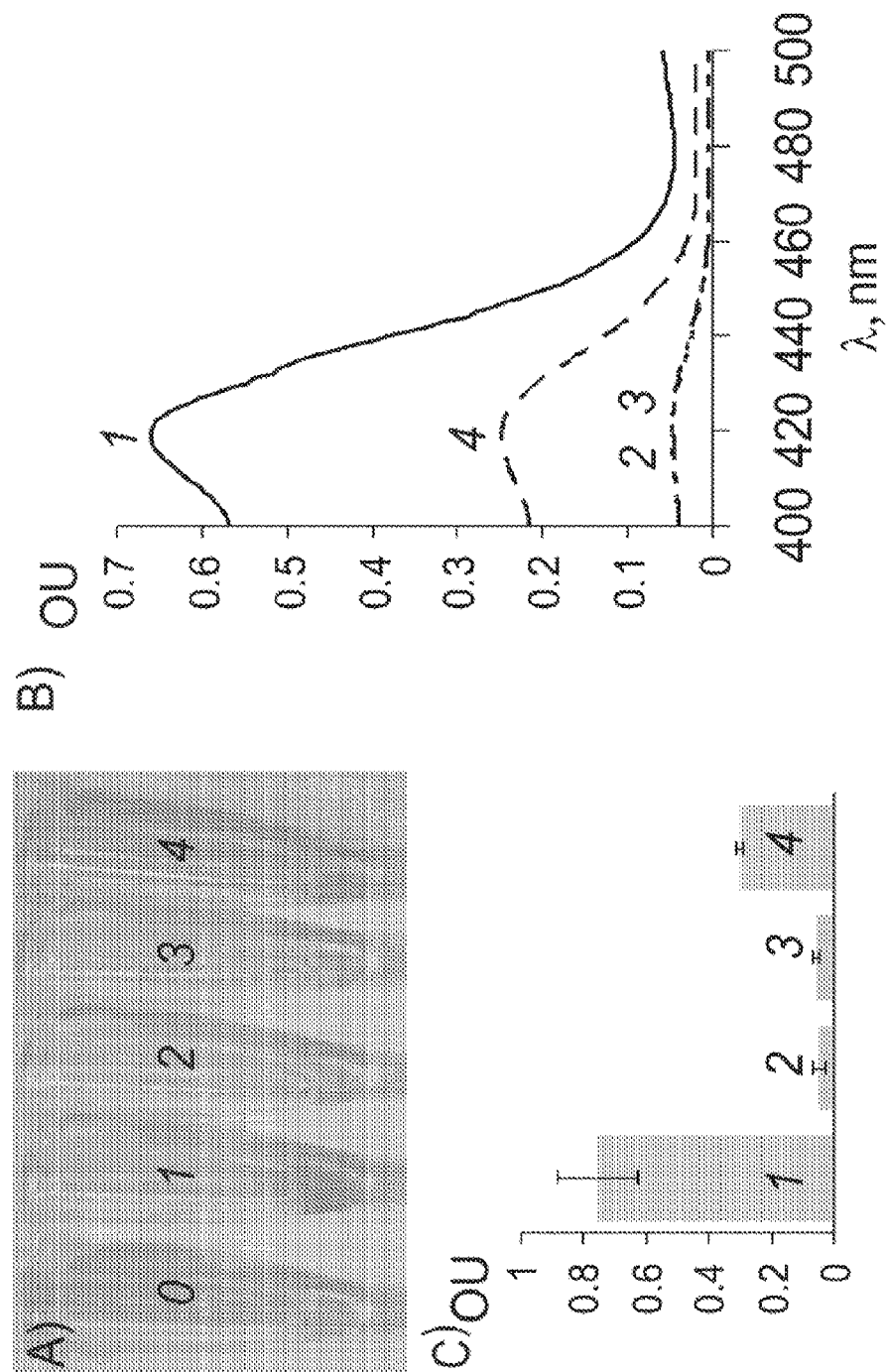
FIG. 4. Binary peroxidase-like DNA enzyme reports SNP in the presence of ABTS. A: Strands α and β in the absence (2), or presence of rs242557-A (3) and rs242557-G (4); Sample 0 contained reaction buffer only; Sample 1: reaction buffer and peroxidase-like DNA enzyme. The samples were incubated 30 min at room temperature. B: Electronic absorption spectra; sample 0 was used as a reference. C: Average optical densities of five independent measurements at 419 nm.

We discovered that DAB can be substituted with another peroxidase substrate, ABTS (2,2'-azino-bis(3-ethylbenz-thiazoline-6-sulphonic acid)) (FIG. 4). However, the S/B ratio was reduced to ~6 in this case, making the color difference less contrasting. Substitution of the triethylene glycol linkers in the structure of strands α and β with dithymidine linkers substantially reduced the intensity of the positive signal in the presence of the specific complementary target (FIG. 4). However, if one of the strands contained dithymidine, while another triethylene glycol linker, the staining was intensive enough to be visualized. This observation suggests that at least one strand of the probe can be composed of purely natural deoxyribonucleotides. Those skilled in the art will be able to make variations of the probe in the linker and analyte binding arms, as described below. For example, more oligonucleotides can be added to the analyte binding arms to form stabilizing stem loop structures.

Binary Oligonucleotide Probe Design

The basic binary probe of the present invention is made of two synthetic, non-naturally occurring, anti-parallel oligonucleotide strands that can be made of DNA or RNA or a combination of both. Each strand of the DNA or RNA probe has a customized fragment that is complementary to a selected target nucleic acid analyte (analyte-binding arm), and a customized fragment complementary to hemin (hemin-binding arms). The analyte- and hemin-binding arms are optionally connected to each other by linker molecules. If there is enough flexibility between the hemin- and analyte-binding arms of each probe strand to form a four-way junction with the target analyte, linkers are not required. For additional sensitivity, preferred embodiments of the binary probes have additional nucleotide sequences added to the free end of the analyte binding arms that are complementary to and hybridize with an internal region of the respective strand to form a stem-loop structure. These additional stem-loop-forming sequences are called structure stabilization arms (SSA), and will be discussed in more detail below.

The newly discovered binary probes have two separate, antiparallel DNA or RNA strands. In some embodiments the probe has several distinct regions on each strand: an analyte-binding arm flanked by an optional flexible linker that is flanked by a hemin-binding arm that binds to hemin conferring on the probe peroxidase-like activity that can be visualized by adding the appropriate substrate to generate a colored product indicating that the analyte has been detected. A separate linker may not be needed if there is enough flexibility in the phosphodiester bonds of the two oligonucleotide strands to permit the probe to form a four-way junction with the analyte. These probes are called "binary" because the two parts of the probe act synergistically and the detection event occurs only when both are hybridized to the analyte. In the absence of a nucleic acid analyte, the strands are dissociated and the probe does not bind the hemin. Addition of a specific DNA/RNA analyte, some or all of which is complementary to the respective analyte-binding arms on the two halves of the probe, results in hybridization of the analyte-binding arms to the corresponding complementary nucleotides on the analyte. The analyte can and often is longer than the combined length of the two analyte-binding arms on the binary probe. When the analyte binds to probe, the two strands of the probe come together and the hemin-binding arms are brought together to enable them to form a G-quadruplex, to which hemin binds giving the BOPP its peroxidase-like activity which indicates that the analyte has been detected.

In one embodiment the BOPP, is made of
 a. the first oligonucleotide strand that has at its 5'-terminus a hemin-binding arm that is flanked by a flexible linker,
 b. a flexible linker that is flanked by a first oligonucleotide analyte-binding arm and
 c. a first oligonucleotide analyte-binding arm that is complementary to and selectively hybridizes with a first region of an oligonucleotide analyte.

The second strand is antiparallel to the first.

In other embodiments the linker may be omitted if there is enough flexibility to permit the probe to form a four-way junction with the analyte. In another embodiment, the oligonucleotide hemin-binding arm on the first oligonucleotide strand includes the sequence 3' gggatggg 5 SEQ ID NO: 3, and the oligonucleotide hemin-binding arm on the second oligonucleotide strand includes 5' gggttggg 3' SEQ ID NO: 4. In other embodiments the oligonucleotide hemin-binding arm on the first oligonucleotide strand comprises 3' ggg 5 SEQ ID NO: 5; and the oligonucleotide hemin-binding arm on the second oligonucleotide strand comprises 5' gggcgggtggg 3' SEQ ID NO: 6, or the oligonucleotide hemin-binding arm on the first oligonucleotide strand comprises 3' gggcgggatggg 5 SEQ ID NO: 7; and the oligonucleotide hemin-binding arm on the second oligonucleotide strand comprises 5' ggg 3' SEQ ID NO: 5.

The analyte-binding arms are customized for each particular analyte. In the examples the probe is entirely DNA, but it can be made of RNA or be a chimera. Likewise the analyte can be DNA, RNA or a chimera. The hemin binding arms are customized to bind to hemin. For optimum selectivity, for example of SNPs, the analyte-binding arm of each strand of the probe ranges from 6-20 nucleotides in length, preferably 10, which make total recognizable analyte fragment 12-40 nucleotides long. Analyte-binding arms of about 10 nucleotides are preferred because a combined length of 20 nucleotides will cover any unique sequence in the genome. It is important to note, that the analyte itself can be of any length from 12-40, to many thousand nucleotides.

The analyte-binding- and hemin-binding arms are separated by flexible linkers that permit the formation of two full-fledged double helixes when the analyte and hemin are bound to the probe. In one embodiment the flexible linker is triethylene glycole. Flexible linkers are also used if the binary probe is made of RNA since RNA will also form a double helix. Nucleotide linkers can also be used if they permit the formation of a double helix. Alternatively there can be enough flexibility in the hemin- and the analyte-binding arms of each strand of the probe so that a linker between the two is not needed in order for the probes to form a four-way junction with target analyte. In the absence of nucleic acid analyte the strands of the probe are unbound in solution. Addition of analyte complementary to the analyte-binding arms triggers the association of the two oligonucleotide strands shown in FIG. 1B, in which the analyte-binding arms bind to the analyte, thereby permitting the hemin-binding arms to form a G-quadruplex that in turn binds to hemin giving the probe its peroxidase-like activity.

The binary probes of the present invention are substantially destabilized by a single mismatched base pair, thereby preventing binding to the hemin. The binary probes thus provide an extraordinary level of selectivity.

The new probes and analytic methods using them have the following major advantages:
 1) Unprecedented high selectivity: the probes and methods permit reliable discrimination of a single base substitution at any position of a 12-20 nucleotide length or target in a DNA/RNA analyte.
 2) High sensitivity: potentially a single nucleic acid molecule can be detected without PCR amplification.
 3) Mild reaction conditions: the method works in buffers close to physiological conditions and at room temperature, thus being potentially applicable in living cells.
 4) Relatively lower costs. The new binary probes enable specific and sensitive nucleic acid analysis and are relatively cheap to make.

DNA probes have an advantage over RNA probes when the analyte is DNA because DNA-DNA duplexes are typically less stable than RNA-DNA duplexes and are therefore more sensitive to SNPs. DNA probes are cheaper also to synthesize and they are more stable to degradation in solution. In those embodiments where the probes are made of RNA oligoribonucleotides, U is substituted for T; otherwise the structures are the same. The analyte binding arms can be DNA, RNA or chimeras; however, the hemin-binding arms are only made of DNA.

It was discovered that sensitivity to a single mismatch or single nucleotide polymorphism in analytes 20 nucleotides long increased if each strand of the probe was designed to form a stem-loop hairpin structure when not bound to analyte. A stem loop structure forms by adding a nucleotide fragment of from about 3-10 nucleotides in length or up to 40 nucleotides in length (called a structure stabilization arm or SSA) to the free end of the analyte-binding arm on each strand of the probe. The added sequences in the SSA are complementary to all or part of the analyte-binding arm. When the complementary sequences in the SSA hybridize to the corresponding sequences in the analyte-binding arm, a stem-loop is formed. The formation of stem-loops represents a conformational constraint that further increases the sensitivity of the binary DNA or RNA probes. SSA can also be added to the free end of the hemin-binding arm if they do not interfere with g-complex formation. When the strands of the probe are present free in solution, i.e., not hybridized to analyte, each dissociated strand of the probe is stabilized by complementary base pairing to itself via the stem loop in the analyte-binding arms. This self-complementary pairing results in a "hairpin loop" structure for the individual strands, which stabilizes the oligonucleotide strands and increases sensitivity. Certain preferred embodiments of the invention are therefore directed to BOPPs where each strand of the probe forms a stem loop structure when the strand is not hybridized to analyte. When analytes are 16 nucleotides long or shorter, adding stem-loops to the analyte-binding arms may not be helpful.

Other embodiments are directed to variations of the binary probe structure that optimize analyte discrimination parameters. Additional changes that may increase the selectivity of the probe include shortening the analyte, for example from 20 to 12 nucleotides, or increasing the reaction temperature to 37° C., which is still within physiologic conditions that can eventually permit analyte analysis in live cells in culture or in vitro. Since the oligonucleotide strands of the binary probe are simple nucleotide sequences they can be made to order by various existing companies such as Integrated DNA Technologies (Coralville, Iowa, USA).

Hybridization Assays and Kits for Making and using the Binary Fluorescent Probes Certain embodiments are also directed to a binary oligonucleotide probe hybridization assay to detect RNA or DNA analyte in a sample containing a heterogeneous mixture of nucleic acids including at least one single stranded analyte molecule that has a known nucleotide sequence. The assay has the following steps:

a) providing a binary oligonucleotide peroxidase probe BOPP described above, wherein the nucleotides in the analyte-binding arms are complementary to the known nucleotide sequence in the analyte, b) adding hemin and a biological sample having the DNA or RNA analyte to the probe to form a mixture, c) maintaining said mixture for a sufficient period of time and under predetermined reaction conditions to allow the analyte to hybridize to the analyte-binding arms on the probe, and for the hemin to bind to the probe, d) adding a peroxidase substrate to the mixture of step c), and e) determining that the analyte is present in the sample if a visible peroxidase substrate reaction product is observed.

Certain embodiments of the invention are directed to truncated forms of the binary probe ("the truncated probe"). In its simplest form each truncated BOPP probe strand has only the hemin-binding arms and flexible linkers, with optional structure stabilization arms internally complementary to a portion of the respective heme-binding arm. The user can customize the analyte-binding arms to suit the target. Certain embodiments are directed to a diagnostic binary oligonucleotide peroxidase probe hybridization assay kit to detect a known RNA or DNA analyte in a sample containing a heterogeneous mixture of nucleic acids, the kit comprising 1. a BOPP (DNA or RNA) probe as described herein that is complementary to and selectively hybridizes with the known DNA or RNA analyte, and 2. Hemin. The kit can further comprise a peroxidase substrate like 3-3'-diaminobenzidine tetrahydrochloride (DAB), 2,2'-azino-bis(3-ethylbenzthiazoline-6-sulphonic acid) (ABTS), 3,3',5,5'-tetramethylbenzidine (TMB), luminol (for chemiluminescence detection) and other standard horseradish peroxidase substrates The new binary probe-based technology requires synthesis of only two short DNA, RNA, or chimeric oligonucleotides with specific analyte-binding arms for each different probe. The hemin-binding arms and the linker can be standard. Standard desalting provides sufficient purity for the oligonucleotides of such lengths. All other components of the probe, such as the hemin-binding arms are universal for all assays. If applied for analysis of many different single nucleotide polymorphisms (SNPs), out of several million existing in human genome, the new approach will offer increased accuracy and the ability to work at moderate physiologic conditions. Since DNA-RNA and DNA-DNA hybrids have different structural parameters, the binary constructions should be customized for RNA in order to obtain highly specific and sensitive recognition of RNA targets.

Diagnostic kits can be prepared having the full BOPP with analyte-binding arms (and optional structure stabilization arms) that are already customized to be complementary to and hybridize with high specificity to a known oligonucleotide analyte. In a preferred embodiment the analyte binding arms recognize the target SNP rs242557-that indicates increased risk of developing Alzheimer's disease.

EXAMPLES

Example 1

A. All buffers and for the stock solutions of oligonucleotides. Oligonucleotides were custom-made by Integrated DNA Technologies, Inc. (Coralville, Iowa). Hydrogen peroxide, 3-3'-diaminobenzidine tetrahydrochloride (DAB), 2,2'-azino-bis(3-ethylbenzthiazoline-6-sulphonic acid) (ABTS), hemin, and HEPES were from Sigma-Aldrich (St. Louis, Mo., USA). Electronic spectra were taken on a Spectrophotometer Ultraspec 3300 (Amersham-Biotech, NJ, USA). The data were processed using Microsoft Excel.

B. SNP typing assay. Binary peroxidase-like DNA enzyme (1 µM both strands) was incubated in the reaction buffer (50 mM HEPES, pH 7.4, 50 mM $MgCl_2$, 20 mM KCl, 120 mM NaCl, 0.03% Triton X-100, 1% DMSO, hemin (125 nM), $H_2O_2$ (1 mM), and DAB or ABTS (1 mM)) in the absence or presence of rs242557-A or rs242557-G. Negative control (sample 0) contained no oligonucleotides; Positive control (sample 1) contained 1 µM proxidase-like DNA enzyme (FIG. 1A). The electronic absorption spectra of the samples were recorded after 30 min of incubation at room temperature. The test tubes were photographed using an Olympus FE-170 digital camera 6 mega pixel.

C. Native PAGE. The reaction mixtures were analyzed in 12% native PAGE containing the reaction buffer. Each reaction mixture was mixed 1:10 with the loading buffer (50% Glycerol, 50 mM HEPES, pH 7.4, 50 mM $MgCl_2$, 20 mM KCl, 120 mM NaCl, 0.03% Triton X-100, 1% DMSO, 0.01% bromphenol, 0.01% xylencyanol). Two microliters of each sample were loaded on the gel and run 1 h at room temperature (200 V) followed by staining with SYBR Gold (Invitrogen, OR) and photographed using Alphaimager 3400 (Alpha Innotech, CA).

D. SNP TYPING USING 2,2'-AZINO-BIS(3-ETHYL-BENZTHIAZOLINE-6-SULPHONIC ACID (ABTS) AS AN OXIDIZABLE SUBSTRATE. ABTS (2,2'-azino-bis(3-ethylbenzthiazoline-6-sulphonic acid) is a commonly used water soluble substrate of hydrogen peroxidases. Therefore, DAB can be substituted with ABTS in the colorimetric assay for SNP. Addition of rs-242557-G made the color of solution containing binary DNA peroxidase probe turn green; this color was visually distinct from the solution containing mismatched rs242557-A or no analyte (compare tubes 4 with 2 and 3, FIG. 2A). The S/B was ~6 (3 and 4, FIGS. 2 B and C). At the same time, the color of the solution peroxidase-like DNA enzyme (positive control) was about 2.5 more intensive than that of sample 4 (compare samples 1 and 4). Therefore, ABTS can replace DAB in the SNP typing assay, but with substantial reduction of S/B (from ~10 to ~6).

Figure 5:
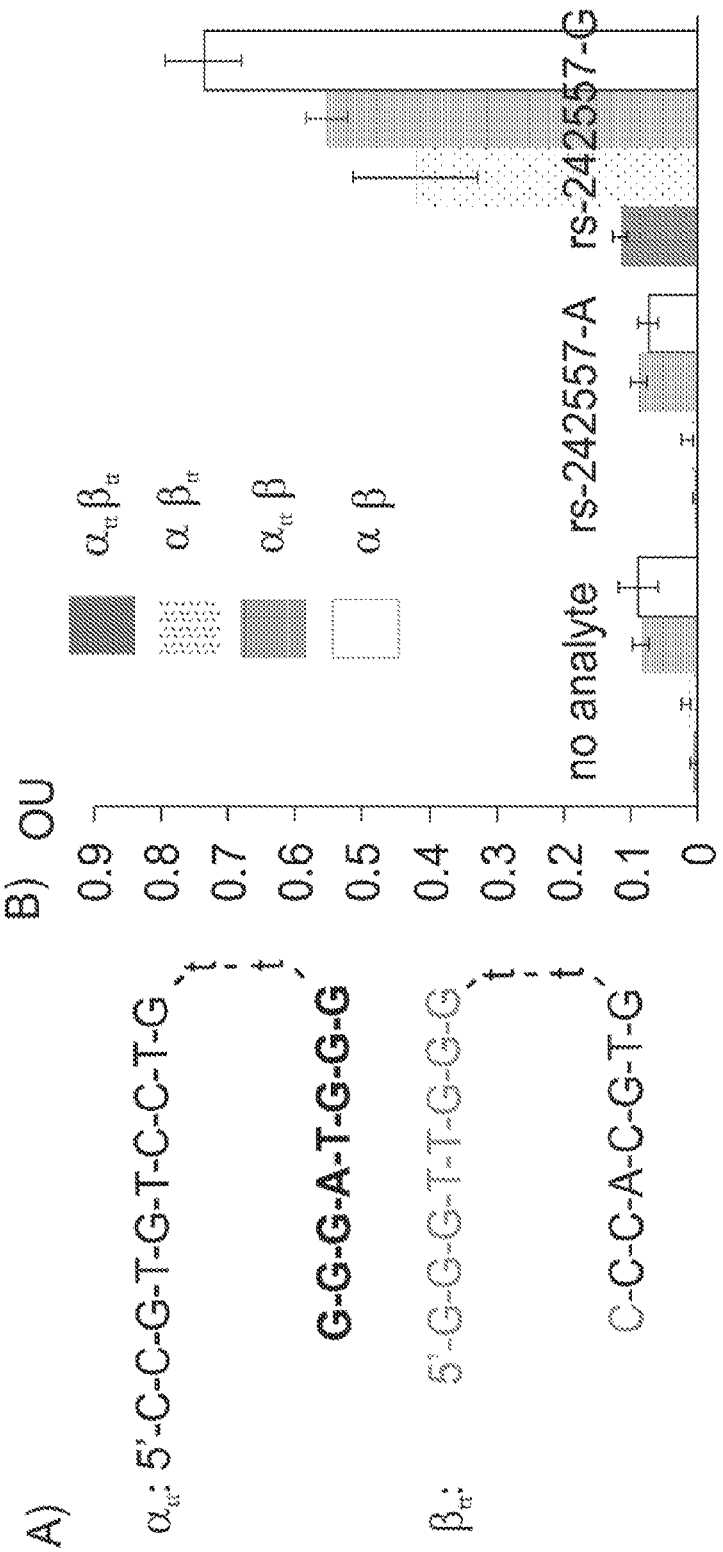
FIG. 5. Binary DNA peroxidase probe containing various linker combinations. A: Sequences of the probe (strands $α_{tt}$ (SEQ ID NO: 11) and $β_{tt}$ (SEQ ID NO: 12)) containing dithymidine linkers (shown in low cases). B: Light absorption of the probes containing different strand combinations in the absence (first group) or presence of rs242557-A (second group), or rs242557-G (third group). The samples contained combinations of 1 µM strands α, β, $α_{tt}$, and $β_{tt}$ (as indicated for each bar type) were incubated 30 min at room temperature in the presence of DAB as an oxidizable substrate followed by the registration of electronic absorption spectrum. The optical densities at 500 nm are represented as average values of four independent measurements.

E. BINARY PEROXIDASE PROBE WITH DITHYMIDINE LINKERS. Triethylene glycol linkers in the sequence of the binary DNA peroxidase probe can be replaced with dithymidine linkers (FIG. 4 A). However, the intensity of the optical signal was reduced about 6 times (from 0.74±0.06 to 0.12±0.01 OU, compare dark grey bar with white bar in third group, panels B). Such a weak color was hardly recognizable by the naked eye (data not shown). At the same time, the probes composed of $\alpha\beta_{tt}$ and $\alpha_{tt}\beta$ generated color intensive enough to be visualized. The highest S/B ratios were found for $\alpha_{tt}\beta_{tt}$ and $\alpha_{tt}\beta$ combinations, ~46 and ~30, respectively, due to a very low background reaction. In all cases the probes were highly selective and generated no signal above the background in the presence of the mismatched analyte (FIG. 5 B, second group of bars). These data suggest that at least one strand of the probe can be composed of purely natural nucleotides. The cost for chemical incorporation of dithymidine linker is almost 50 times lower than that of the triethylene glycol linker. Therefore, using nucleotide linker containing constructs may further reduce the assay cost.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference. Although specific terms are employed, they are used as in the art unless otherwise indicated.

REFERENCES (1) (a) Budowle, B. *Forensic Sci. Int.* 2004, 146, 139-142. (b) Piunno, P. A.; Krull, U. J. *Anal. Bioanal. Chem.* 2005, 381, 1004-1011. (c) Kwok, P.-Y. *Annu. Rev. Genomics. Hum. Genet.* 2001, 2, 235-258. (d) Hacia, J. G. *Nat. Genet.* 1999, 21, 42-47. (e) Hahn, S.; Mergenthaler, S.; Zimmermann, B.; Holzgreve, W. *Bioelectrochemistry* 2005, 67, 151-154. (f) Ng, J. K.; Liu, W. T. *Anal. Bioanal. Chem.* 2006, 386, 427-434. (g) Kim, S.; Misra, A. *Annu. Rev. Biomed. Eng.* 2007, 9, 289-320.

(2) (a) Xu, Y.; Karalkar N. B.; Kool, E. T. *Nat. Biotechnol.*, 2001, 19, 148-152; (b) Sando, S.; Abe H. Kool E. T., J. *Am. Chem. Soc.*, 2004, 126, 1081-1087; (c) Bichenkova, E. V.; Savage, H. E.; Sardarian, A. R.; Douglas, K. T. *Biochem. Biophys. Res. Commun.*, 2005, 332, 956-964; (d) Kolpashchikov, D. M. *J. Am. Chem. Soc.*, 2005, 127, 12442-12443; (e) Kolpashchikov, D. M. *J. Am. Chem. Soc.* 2006, 128, 10625-10628; (f) Marti, A. A.; Li, X.; Jockusch, S.; Li, Z.; Raveendra B.; Kalachikov, S.; Russo, J. J.; Morozova, I.; Puthanveettil, S. V: Ju J.; Turro N. J. *Nucleic Acids Res.* 2006, 34, 3161-3168; (g) Kitamura, Y.; Ihara, T.; Tsujimura, Y.; Osawa, Y.; Tazaki, M.; Jyo, A.; *Anal. Biochem.* 2006, 359, 259-61; (h) Kolpashchikov, D. M. *ChemBioChem.*, 2007, 8, 2039-2042.

(3) (a) Li, Y.; Geyer, C. R.; Sen, D. *Biochemistry,* 1996, 35, 6911-6922.

(4) (b) Travascio, P.; Li, Y.; Sen D. *Chem. Biol.* 1998, 5, 505-517. (c) Travascio, P.; Bennet, A. J.; Wang, D. Y.; Sen, D. *Chem. Biol.* 1999, 6, 779-787.

(5) (a) Xiao, Y.; Pavlov, V.; Niazov, T.; Dishon, A.; Kotler, M.; Willner, I. *J Am Chem Soc.* 2004, 126, 7430-7431. (b) Li, D.; Shlyahovsky, B.; Elbaz, J.; Willner, I.; *Biosens Bioelectron.* 2007, 22, 2570-2576; (c) Pavlov, V.; Xiao, Y.; Gill R.; Dishon, A.; Kotler, M.; Willner, I. *Anal. Chem.* 2004, 76, 2152-2156; (d) Xiao, Y.; Pavlov, V.; Gill R.; Bourenko, T.; Willner, I. *Chembiochem.* 2004, 5, 374-379.

(6) Myers, A. J.; Kaleem, M.; Marlowe, L.; Pittman, A. M.; Lees A. J.; Fung, H. C.; Duckworth, J.; Leung, D.; Gibson, A.; Morris, C. M.; de Silva, R.; Hardy, J. *Human Mol. Gen.* 2005, 14, 2399-2404.

(7) (a) Mirkin, C. A.; Rossi, N. L. *Chem. Rev.* 2005, 105, 1547-1562. (b) Sato, K.; Hosokawa, K.; Maeda, M. *Anal. Sci.,* 2007, 23, 17-20. (c) Murphy, D.; O'Brien, P.; Redmond, G. *The Analyst,* 2004, 129, 970-974.

Also:
1. Kolpashchikov D. M. (2008). "Split DNA enzyme for visual single nucleotide polymorphism typing." JACS, 130, 2934-2935.
2. Kolpashchikov D. M. (2007) "A binary deoxyribozyme for nucleic acid analysis." ChemBioChem 8, 2039-2042.
3. Kolpashchikov D. M. (2006) "A binary DNA probe for highly specific nucleic acid recognition." JACS, 128, 10625-10628.
4. Kolpashchikov D. M. (2005) "Binary malachite green aptamer for fluorescent detection of nucleic acids. JACS, 127, 12442-12443.
5. Kolpashchikov D. M., Stojanovic M. N. (2005) "Boolean control of aptameric binding states." JACS, 127, 11348-11341.
6. Kolpashchikov D. M, Honda A., Ishihama A. (2004) Structure-function relationships of influenza virus RNA polymerase: primer-binding site on PB1 subunit. Biochemistry, 43, 5882-5887.
7. Kolpashchikov D. M. (2003) "Superaffinity labeling of proteins: approaches and techniques." J. Biomol. Struct. Dyn., 21, 55-64.

What is claimed is:

1. A non-naturally occurring binary oligonucleotide peroxidase
    probe (BOPP) for detecting a single stranded oligonucleotide analyte comprising two oligonucleotide strands, wherein
    1. a first oligonucleotide strand comprises:
        a. at its 5'-terminus an oligonucleotide hemin-binding arm that is flanked by a first oligonucleotide analyte binding arm, and
        b. at its 3'-terminus, the first oligonucleotide analyte binding arm that is complementary to and selectively hybridizes with a first unique region of the oligonucleotide analyte;
    2. a second oligonucleotide strand comprises:
        a. at its 3'-terminus an oligonucleotide hemin-binding arm that is flanked by a second oligonucleotide analyte binding arm, and
        b. at its 5'-terminus, the second oligonucleotide analyte binding arm that is complementary to and selectively hybridizes with a second unique region of the oligonucleotide analyte that is adjacent to the first unique region; and
    3. a.) one of either the first or the second oligonucleotide strands comprises a non-nucleotide linker while the other strand comprises a nucleotide linker that is at least two nucleotides long between the oligonucleotide hemin-binding arm and the oligonucleotide analyte binding arm, or b.) both the first and the second oligonucleotide strands comprise a non-nucleotide linker between the oligonucleotide hemin-binding arm and the oligonucleotide analyte binding arm.

2. The non-naturally occurring binary oligonucleotide peroxidase probe (BOPP) of claim 1, wherein the oligonucleotide hemin-binding arm on the first oligonucleotide strand comprises SEQ ID NO: 3, and the oligonucleotide hemin-binding arm on the second oligonucleotide strand comprises SEQ ID NO: 4.

3. The non-naturally occurring binary oligonucleotide peroxidase probe (BOPP) of claim 1, wherein the oligonucleotide hemin-binding arm on the first oligonucleotide strand comprises SEQ ID NO: 5, and the oligonucleotide hemin-binding arm on the second oligonucleotide strand comprises SEQ ID NO: 6.

4. The non-naturally occurring binary oligonucleotide peroxidase probe (BOPP) of claim 1, wherein the oligonucleotide hemin-binding arm on the first oligonucleotide strand comprises SEQ ID NO: 7, and the oligonucleotide hemin-binding arm on the second oligonucleotide strand comprises SEQ ID NO: 5.

5. The non-naturally occurring binary oligonucleotide peroxidase probe (BOPP) of claim 1, wherein the oligonucleotides in the hemin-binding arm on the first and second oligonucleotide strands form a guanine quadruplex when the first and second oligonucleotide analyte binding arms of the probe are bound to the analyte.

6. The non-naturally occurring binary oligonucleotide peroxidase probe (BOPP) of claim 5, wherein hemin is bound to the guanine quadruplex, thereby imparting peroxidase-like activity to the probe.

7. The non-naturally occurring binary oligonucleotide peroxidase probe (BOPP) of claim 6, wherein the peroxidase-like activity of the hemin bound to the guanine quadruplex is greater than the peroxidase-like activity of unbound hemin.

8. The non-naturally occurring binary oligonucleotide peroxidase probe (BOPP) of claim 6, wherein the guanine quadruplex binds covalently to hemin.

9. The non-naturally occurring binary oligonucleotide peroxidase probe (BOPP) of claim 6, wherein the guanine quadruplex binds noncovalently to hemin.

10. The non-naturally occurring binary oligonucleotide peroxidase probe (BOPP) of claim 1, wherein the oligonucleotide analyte binding arms and the hemin-binding arms of the probe are DNA oligonucleotides.

11. The non-naturally occurring binary oligonucleotide peroxidase probe (BOPP) of claim 1, wherein the oligonucleotide analyte binding arms and the hemin-binding arms of the probe are RNA oligonucleotides.

12. The non-naturally occurring binary oligonucleotide peroxidase probe (BOPP) of claim 1, wherein the non-nucleotide linker is oligoethylene glycol.

13. The non-naturally occurring binary oligonucleotide peroxidase probe (BOPP) of claim 1, wherein the linkers on the first and second strands are flexible and permit the formation of a double helix when the analyte is bound to the analyte binding arms.

14. The non-naturally occurring binary oligonucleotide peroxidase probe (BOPP) of claim 1, wherein the oligonucleotide analyte is DNA.

15. The non-naturally occurring binary oligonucleotide peroxidase probe (BOPP) of claim 1, wherein the oligonucleotide analyte is RNA.

16. The non-naturally occurring binary oligonucleotide peroxidase probe (BOPP) of claim 1, wherein the oligonucleotide analyte is a chimera of RNA and DNA.

17. The non-naturally occurring binary oligonucleotide peroxidase probe (BOPP) of claim 1, wherein the analyte binding arms each comprise from about 6 to about 20 nucleotides, preferably from about 8 to about 10 nucleotides.

18. The non-naturally occurring binary oligonucleotide peroxidase probe (BOPP) of claim 1, wherein from about 3-20 additional nucleotides are added to the free end of the oligonucleotide analyte binding arms on the first and second oligonucleotide strands, which additional nucleotides are complementary to and hybridize with nucleotides in the respective antiparallel oligonucleotide analyte binding arms thereby forming a stem-loop structure when the first and second oligonucleotide strands are not hybridized to the oligonucleotide analyte.

19. The non-naturally occurring binary oligonucleotide peroxidase probe (BOPP) of claim 1, wherein the analyte binding arms are complementary to and selectively hybridize with SEQ ID NO: 1 nucleic acid sequence.

20. A diagnostic binary oligonucleotide peroxidase probe hybridization assay kit to detect a single stranded nucleic acid analyte in a sample containing a heterogeneous mixture of nucleic acids, the kit comprising:
    a. the non-naturally occurring binary oligonucleotide peroxidase probe of claim 1, and
    b. hemin.

21. The kit of claim 20, further comprising a peroxidase substrate that is a member selected from the group comprising 3-3'-diaminobenzidine tetrahydrochloride (DAB), and 2,2'-azino-bis(3-ethylbenzthiazoline-6-sulphonic acid) (ABTS), 3,3',5,5'-Tetramethylbenzidine (TMB), luminol (for chemiluminescence detection) and horseradish peroxidase substrates.

* * * * *